United States Patent
Mulier et al.

(10) Patent No.: US 7,422,588 B2
(45) Date of Patent: Sep. 9, 2008

(54) PEN-TYPE ELECTROSURGICAL INSTRUMENT

(75) Inventors: Peter M. J. Mulier, Stillwater, MN (US); Michael F. Hoey, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/635,166

(22) Filed: Dec. 7, 2006

(65) Prior Publication Data

US 2007/0208332 A1  Sep. 6, 2007

Related U.S. Application Data

(63) Continuation of application No. 11/230,839, filed on Sep. 20, 2005, now Pat. No. 7,166,105, which is a continuation of application No. 10/883,178, filed on Jul. 1, 2004, now Pat. No. 6,949,098, which is a continuation of application No. 10/411,921, filed on Apr. 11, 2003, now Pat. No. 6,764,487, which is a continuation of application No. 09/955,496, filed on Sep. 18, 2001, now Pat. No. 6,585,732, which is a continuation of application No. 09/580,228, filed on May 26, 2000, now Pat. No. 6,358,248, which is a continuation of application No. 09/236,034, filed on Jan. 22, 1999, now abandoned, which is a continuation of application No. 08/556,784, filed on Nov. 2, 1995, now Pat. No. 5,897,553, which is a continuation-in-part of application No. 08/393,082, filed on Feb. 22, 1995, now Pat. No. 6,063,081.

(51) Int. Cl.
 *A61B 18/14* (2006.01)

(52) U.S. Cl. .............. 606/41; 606/45; 606/46; 606/49; 607/99

(58) Field of Classification Search .......... 606/32, 606/41, 49

See application file for complete search history.

(56) References Cited

U.S. PATENT DOCUMENTS 623,022 A  4/1899  Johnson (Continued)

FOREIGN PATENT DOCUMENTS

DE  1007960  5/1957

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Lee S Cohen
(74) *Attorney, Agent, or Firm*—Mike Jaro; Jeffrey J. Hohenshell

(57) ABSTRACT

An electrocautery device is disclosed. In accordance with one aspect of the invention, the electrocautery electrode/tip is provided with a hollow, conductive tube terminating at its distal end in a ball point type tip. Fluid, preferably conductive fluid, is applied to the proximal end of the hollow electrode/tip, and expelled from the distal end thereof during electrocautery. The ball point distal tip allows the distal tip to be directly applied to the tissue and "rolled" or slid along the tissue. This allows the distal tip to be moved across the tissue without dragging or snagging on the tissue. In addition, the conductive fluid expelled from the distal tip further lubricates the distal tip as it moves across the tissue. If conductive fluid is used, the conductive fluid emanating from the electrode/tip conducts the RF electrocautery energy away from the distal tip so that it is primarily the fluid, rather than the distal tip that actually accomplishes the cauterizing of tissue. That is, the fluid serves as a "virtual" electrocautery electrode. Since it is the fluid, rather than the distal tip that cauterizes, coagulates and ablates, no burns or perforations are made to the tissue, reducing the amount of debris at the site. Also, the flow of fluid through the electrode/tip tends to keep the distal tip clean and cool.

7 Claims, 2 Drawing Sheets

U.S. PATENT DOCUMENTS

| | | |
|---|---|---|
| 1,735,271 A | 11/1929 | Groff |
| 2,102,270 A | 12/1937 | Mortimer |
| 2,275,167 A | 3/1942 | Bierman |
| 2,888,928 A | 6/1959 | Seiger |
| 3,163,166 A | 12/1964 | Brent et al. |
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,241 A | 8/1975 | Allen |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,037,590 A | 7/1977 | Dohring et al. |
| 4,061,135 A | 12/1977 | Widran et al. |
| 4,063,560 A | 12/1977 | Thomas et al. |
| 4,072,152 A | 2/1978 | Linehan |
| 4,074,718 A | 2/1978 | Morrison |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,301,802 A | 11/1981 | Poler |
| 4,307,720 A | 12/1981 | Weber, Jr. |
| 4,326,529 A | 4/1982 | Doss et al. |
| 4,377,168 A | 3/1983 | Rzasa et al. |
| 4,506,680 A | 3/1985 | Stokes |
| 4,519,389 A | 5/1985 | Gudkin et al. |
| 4,532,924 A | 8/1985 | Auth et al. |
| 4,567,890 A | 2/1986 | Ohta et al. |
| 4,598,698 A | 7/1986 | Siegmund |
| 4,601,290 A | 7/1986 | Effron et al. |
| 4,602,628 A | 7/1986 | Allen |
| 4,641,649 A | 2/1987 | Walinsky et al. |
| 4,664,110 A | 5/1987 | Schanzlin |
| 4,674,498 A | 6/1987 | Stasz |
| 4,674,499 A | 6/1987 | Pao |
| 4,682,596 A | 7/1987 | Bales et al. |
| 4,736,749 A | 4/1988 | Lundback |
| 4,748,979 A | 6/1988 | Hershenson |
| 4,779,611 A | 10/1988 | Grooters et al. |
| 4,802,475 A | 2/1989 | Weshahy |
| 4,802,476 A | 2/1989 | Noerenberg et al. |
| 4,815,470 A | 3/1989 | Curtis et al. |
| 4,832,048 A | 5/1989 | Cohen |
| 4,850,353 A | 7/1989 | Stasz et al. |
| 4,862,890 A | 9/1989 | Stasz et al. |
| 4,869,248 A | 9/1989 | Narula |
| 4,872,346 A | 10/1989 | Kelly-Fry et al. |
| 4,896,671 A | 1/1990 | Cunningham et al. |
| 4,916,922 A | 4/1990 | Mullens |
| 4,917,095 A | 4/1990 | Fry et al. |
| 4,920,982 A | 5/1990 | Goldstein |
| 4,931,047 A | 6/1990 | Broadwin et al. |
| 4,932,952 A | 6/1990 | Wojciechowicz |
| 4,936,281 A | 6/1990 | Stasz |
| 4,943,290 A | 7/1990 | Rexroth et al. |
| 4,946,460 A | 8/1990 | Merry et al. |
| 4,966,597 A | 10/1990 | Cosman |
| 4,976,711 A | 12/1990 | Parins et al. |
| 4,977,902 A | 12/1990 | Sekino et al. |
| 4,979,948 A | 12/1990 | Geddes et al. |
| 4,985,030 A | 1/1991 | Melzer et al. |
| 5,007,908 A | 4/1991 | Rydell |
| 5,013,312 A | 5/1991 | Parins et al. |
| 5,029,574 A | 7/1991 | Shimamura et al. |
| 5,044,165 A | 9/1991 | Linner et al. |
| 5,056,517 A | 10/1991 | Fenici |
| 5,057,107 A | 10/1991 | Parins et al. |
| 5,071,419 A | 12/1991 | Rydell et al. |
| 5,078,713 A | 1/1992 | Varney |
| 5,078,717 A | 1/1992 | Parins et al. |
| 5,080,102 A | 1/1992 | Dory |
| 5,080,660 A | 1/1992 | Buelina |
| 5,083,565 A | 1/1992 | Parins |
| 5,087,256 A | 2/1992 | Taylor et al. |
| 5,098,431 A | 3/1992 | Rydell |
| 5,100,388 A | 3/1992 | Behl et al. |
| 5,108,390 A | 4/1992 | Potocky et al. |
| 5,122,137 A | 6/1992 | Lennox |
| 5,122,138 A | 6/1992 | Manwaring |
| 5,125,928 A | 6/1992 | Parins et al. |
| 5,129,396 A | 7/1992 | Rosen et al. |
| 5,147,355 A | 9/1992 | Friedman et al. |
| 5,150,717 A | 9/1992 | Rosen et al. |
| 5,167,659 A | 12/1992 | Ohtomo et al. |
| 5,171,311 A | 12/1992 | Rydell et al. |
| 5,178,133 A | 1/1993 | Pena |
| 5,178,618 A | 1/1993 | Kandarpa |
| 5,188,635 A | 2/1993 | Radtke |
| 5,190,541 A | 3/1993 | Abele et al. |
| 5,192,280 A | 3/1993 | Parins |
| 5,195,959 A | 3/1993 | Smith |
| 5,197,963 A | 3/1993 | Parins |
| 5,197,964 A | 3/1993 | Parins |
| 5,207,674 A | 5/1993 | Hamilton |
| 5,215,103 A | 6/1993 | Desai |
| 5,217,460 A | 6/1993 | Knoepfler |
| 5,217,860 A | 6/1993 | Fahy et al. |
| 5,220,927 A | 6/1993 | Astrahan et al. |
| 5,222,501 A | 6/1993 | Ideker et al. |
| 5,224,943 A | 7/1993 | Goddard |
| 5,228,923 A | 7/1993 | Hed |
| 5,230,349 A | 7/1993 | Langberg |
| 5,231,995 A | 8/1993 | Desai |
| 5,232,516 A | 8/1993 | Hed |
| 5,242,441 A | 9/1993 | Avitall |
| 5,242,442 A | 9/1993 | Hirschfeld |
| 5,254,116 A | 10/1993 | Baust et al. |
| 5,263,493 A | 11/1993 | Avitall |
| 5,269,291 A | 12/1993 | Carter |
| 5,269,781 A | 12/1993 | Hewell, III |
| 5,275,595 A | 1/1994 | Dobak, III |
| 5,277,201 A | 1/1994 | Stern |
| 5,277,696 A | 1/1994 | Hagen |
| 5,281,213 A | 1/1994 | Milder et al. |
| 5,281,215 A | 1/1994 | Milder |
| 5,281,217 A | 1/1994 | Edwards et al. |
| 5,281,218 A | 1/1994 | Imran |
| 5,282,799 A | 2/1994 | Rydell |
| 5,290,286 A | 3/1994 | Parins |
| 5,295,484 A | 3/1994 | Marcus et al. |
| 5,300,087 A | 4/1994 | Knoepfler |
| 5,309,896 A | 5/1994 | Moll et al. |
| 5,313,943 A | 5/1994 | Houser et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |

| | | | | | |
|---|---|---|---|---|---|
| 5,342,357 A | 8/1994 | Nardella | 5,575,810 A | 11/1996 | Swanson et al. |
| 5,348,554 A | 9/1994 | Imran et al. | 5,578,007 A | 11/1996 | Imran |
| 5,353,783 A | 10/1994 | Nakao et al. | 5,582,609 A | 12/1996 | Swanson et al. |
| 5,354,258 A | 10/1994 | Dory | 5,584,872 A | 12/1996 | LaFontaine et al. |
| 5,361,752 A | 11/1994 | Moll et al. | 5,588,432 A | 12/1996 | Crowley |
| 5,383,876 A | 1/1995 | Nardella | 5,590,657 A | 1/1997 | Cain et al. |
| 5,385,148 A | 1/1995 | Lesh et al. | 5,595,183 A | 1/1997 | Swanson et al. |
| 5,395,312 A | 3/1995 | Desai | 5,605,539 A | 2/1997 | Buelna et al. |
| 5,395,363 A | 3/1995 | Billings | 5,607,462 A | 3/1997 | Imran |
| 5,396,887 A | 3/1995 | Imran | 5,617,854 A | 4/1997 | Munsif |
| 5,397,304 A | 3/1995 | Truckai | 5,630,837 A | 5/1997 | Crowley |
| 5,398,683 A | 3/1995 | Edwards et al. | 5,634,924 A | 6/1997 | Turkel et al. |
| 5,400,770 A | 3/1995 | Nakao et al. | 5,637,090 A | 6/1997 | McGee et al. |
| 5,400,783 A | 3/1995 | Pomeranz et al. | 5,637,110 A | 6/1997 | Pennybacker et al. |
| 5,401,272 A | 3/1995 | Perkins | 5,640,995 A | 6/1997 | Packard et al. |
| 5,403,309 A | 4/1995 | Coleman et al. | 5,643,197 A | 7/1997 | Brucker et al. |
| 5,403,311 A | 4/1995 | Abele et al. | 5,653,692 A | 8/1997 | Masterson et al. |
| 5,405,376 A | 4/1995 | Mulier et al. | 5,656,029 A | 8/1997 | Imran et al. |
| 5,409,483 A | 4/1995 | Campbell et al. | 5,658,278 A | 8/1997 | Imran et al. |
| 5,423,807 A | 6/1995 | Milder | 5,660,836 A | 8/1997 | Knowlton |
| 5,423,811 A | 6/1995 | Imran et al. | 5,671,747 A | 9/1997 | Connor |
| 5,427,119 A | 6/1995 | Swartz et al. | 5,673,695 A | 10/1997 | McGee et al. |
| 5,431,649 A | 7/1995 | Mulier | 5,676,662 A | 10/1997 | Fleischhacker et al. |
| 5,433,708 A | 7/1995 | Nichols et al. | 5,676,692 A | 10/1997 | Sanghvi et al. |
| 5,435,308 A | 7/1995 | Gallup et al. | 5,676,693 A | 10/1997 | LaFontaine |
| 5,437,651 A | 8/1995 | Todd et al. | 5,678,550 A | 10/1997 | Bassen et al. |
| 5,437,662 A | 8/1995 | Nardella | 5,680,860 A | 10/1997 | Imran |
| 5,441,498 A | 8/1995 | Perkins | 5,681,278 A | 10/1997 | Igo et al. |
| 5,443,463 A | 8/1995 | Stern et al. | 5,681,282 A | 10/1997 | Eggers et al. |
| 5,443,470 A | 8/1995 | Stern et al. | 5,681,308 A | 10/1997 | Edwards et al. |
| 5,450,843 A | 9/1995 | Moll et al. | 5,683,366 A | 11/1997 | Eggers et al. |
| 5,452,582 A | 9/1995 | Longsworth | 5,683,384 A | 11/1997 | Gough et al. |
| 5,452,733 A | 9/1995 | Sterman et al. | 5,687,723 A | 11/1997 | Avitall |
| 5,458,596 A | 10/1995 | Lax et al. | 5,687,737 A | 11/1997 | Branham et al. |
| 5,458,597 A | 10/1995 | Edwards et al. | 5,688,267 A | 11/1997 | Panescu et al. |
| 5,462,521 A | 10/1995 | Brucker et al. | 5,690,611 A | 11/1997 | Swartz et al. |
| 5,462,545 A | 10/1995 | Wang et al. | 5,697,281 A | 12/1997 | Eggers et al. |
| 5,465,717 A | 11/1995 | Imran et al. | 5,697,536 A | 12/1997 | Eggers et al. |
| 5,469,853 A | 11/1995 | Law et al. | 5,697,882 A | 12/1997 | Eggers et al. |
| 5,472,441 A | 12/1995 | Edwards et al. | 5,697,925 A | 12/1997 | Taylor |
| 5,472,876 A | 12/1995 | Fahy | 5,697,927 A | 12/1997 | Imran et al. |
| 5,478,309 A | 12/1995 | Sweezer et al. | 5,697,928 A | 12/1997 | Walcott et al. |
| 5,478,330 A | 12/1995 | Imran et al. | 5,713,942 A | 2/1998 | Stern |
| 5,486,193 A | 1/1996 | Bourne et al. | 5,716,389 A | 2/1998 | Walinsky et al. |
| 5,487,385 A | 1/1996 | Avitall | 5,718,241 A | 2/1998 | Ben-Haim et al. |
| 5,487,757 A | 1/1996 | Truckai et al. | 5,718,701 A | 2/1998 | Shai et al. |
| 5,496,312 A | 3/1996 | Klicek | 5,720,775 A | 2/1998 | Larnard |
| 5,497,774 A | 3/1996 | Swartz et al. | 5,722,400 A | 3/1998 | Ockuly et al. |
| 5,498,248 A | 3/1996 | Milder | 5,722,402 A | 3/1998 | Swanson et al. |
| 5,500,012 A | 3/1996 | Brucker et al. | 5,730,074 A | 3/1998 | Peter |
| 5,505,730 A | 4/1996 | Edwards | 5,730,127 A | 3/1998 | Avitall |
| 5,514,130 A | 5/1996 | Baker | 5,730,704 A | 3/1998 | Avitall |
| 5,516,505 A | 5/1996 | McDow | 5,733,280 A | 3/1998 | Avitall |
| 5,520,682 A | 5/1996 | Baust et al. | 5,735,280 A | 4/1998 | Sherman et al. |
| 5,522,870 A | 6/1996 | Ben-Zion | 5,735,290 A | 4/1998 | Sterman et al. |
| 5,536,267 A | 7/1996 | Edwards et al. | 5,735,846 A | 4/1998 | Panescu et al. |
| 5,542,928 A | 8/1996 | Evans et al. | 5,746,739 A | 5/1998 | Sutter |
| 5,545,195 A | 8/1996 | Lennox et al. | 5,755,753 A | 5/1998 | Knowlton |
| 5,545,200 A | 8/1996 | West et al. | 5,755,760 A | 5/1998 | Maguire et al. |
| 5,549,661 A | 8/1996 | Kordis et al. | 5,767,693 A | 6/1998 | Hastings et al. |
| 5,555,883 A | 9/1996 | Avitall | 5,769,846 A | 6/1998 | Edwards et al. |
| 5,558,671 A | 9/1996 | Yates | 5,782,828 A | 7/1998 | Chen et al. |
| 5,560,362 A | 10/1996 | Sliwa, Jr. et al. | 5,785,705 A | 7/1998 | Baker |
| 5,562,703 A | 10/1996 | Desai | 5,785,706 A | 7/1998 | Bednarek |
| 5,562,720 A | 10/1996 | Stern et al. | 5,788,636 A | 8/1998 | Curley |
| 5,564,440 A | 10/1996 | Swartz et al. | 5,792,140 A | 8/1998 | Tu et al. |
| 5,569,241 A | 10/1996 | Edwards | 5,797,960 A | 8/1998 | Stevens et al. |
| 5,569,242 A | 10/1996 | Lax et al. | 5,798,960 A | 8/1998 | Hughes |
| 5,571,088 A | 11/1996 | Lennox et al. | 5,800,413 A | 9/1998 | Swartz et al. |
| 5,571,215 A | 11/1996 | Sterman et al. | 5,800,428 A | 9/1998 | Nelson et al. |
| 5,573,532 A | 11/1996 | Chang et al. | 5,800,482 A | 9/1998 | Pomeranz et al. |
| 5,575,766 A | 11/1996 | Swartz et al. | 5,810,802 A | 9/1998 | Panescu et al. |
| 5,575,788 A | 11/1996 | Baker et al. | 5,823,956 A | 10/1998 | Roth et al. |

| | | | | | | |
|---|---|---|---|---|---|---|
| 5,827,216 | A | 10/1998 | Igo et al. | 6,241,754 | B1 | 6/2001 | Swanson |
| 5,833,703 | A | 11/1998 | Manushakian | 6,245,061 | B1 | 6/2001 | Panescu et al. |
| 5,836,947 | A | 11/1998 | Fleischman et al. | 6,245,064 | B1 | 6/2001 | Lesh et al. |
| 5,840,030 | A | 11/1998 | Ferek-Petric et al. | 6,245,065 | B1 | 6/2001 | Panescu et al. |
| 5,844,349 | A | 12/1998 | Oakley et al. | 6,251,092 | B1 | 6/2001 | Qin et al. |
| 5,846,187 | A | 12/1998 | Wells et al. | 6,251,128 | B1 | 6/2001 | Knopp et al. |
| 5,846,191 | A | 12/1998 | Wells et al. | 6,270,471 | B1 | 8/2001 | Hechel et al. |
| 5,849,028 | A | 12/1998 | Chen | 6,293,943 | B1 | 9/2001 | Panescu et al. |
| 5,855,614 | A | 1/1999 | Stevens et al. | 6,296,619 | B1 | 10/2001 | Brisken et al. |
| 5,860,974 | A | 1/1999 | Abele | 6,302,880 | B1 | 10/2001 | Schaer |
| 5,871,523 | A | 2/1999 | Fleischman et al. | 6,302,903 | B1 | 10/2001 | Mulier et al. |
| 5,871,525 | A | 2/1999 | Edwards et al. | 6,311,692 | B1 | 11/2001 | Vaska et al. |
| 5,873,845 | A | 2/1999 | Cline et al. | 6,312,383 | B1 | 11/2001 | Lizzi et al. |
| 5,876,399 | A | 3/1999 | Chia et al. | 6,314,962 | B1 | 11/2001 | Vaska et al. |
| 5,879,295 | A | 3/1999 | Li et al. | 6,314,963 | B1 | 11/2001 | Vaska et al. |
| 5,879,296 | A | 3/1999 | Ockuly et al. | 6,315,777 | B1 | 11/2001 | Comben |
| 5,881,732 | A | 3/1999 | Sung et al. | 6,325,797 | B1 | 12/2001 | Stewart et al. |
| 5,882,346 | A | 3/1999 | Pomeranz et al. | 6,328,736 | B1 | 12/2001 | Mulier |
| 5,885,278 | A | 3/1999 | Fleischman | 6,332,881 | B1 | 12/2001 | Carner et al. |
| 5,893,848 | A | 4/1999 | Negus et al. | 6,358,248 | B1 | 3/2002 | Mulier |
| 5,895,417 | A | 4/1999 | Pomeranz et al. | 6,361,531 | B1 | 3/2002 | Hissong |
| 5,897,553 | A | 4/1999 | Mulier et al. | 6,364,876 | B1 | 4/2002 | Erb et al. |
| 5,897,554 | A | 4/1999 | Chia et al. | 6,368,275 | B1 | 4/2002 | Sliwa et al. |
| 5,899,898 | A | 5/1999 | Arless et al. | 6,371,955 | B1 | 4/2002 | Fuimaono et al. |
| 5,899,899 | A | 5/1999 | Arless et al. | 6,383,151 | B1 | 5/2002 | Diederich et al. |
| 5,902,289 | A | 5/1999 | Swartz et al. | 6,385,472 | B1 | 5/2002 | Hall et al. |
| 5,904,711 | A | 5/1999 | Flom et al. | 6,398,792 | B1 | 6/2002 | O'Connor |
| 5,906,580 | A | 5/1999 | Kline-Schoder et al. | 6,409,722 | B1 | 6/2002 | Hoey |
| 5,906,587 | A | 5/1999 | Zimmon | 6,413,254 | B1 | 7/2002 | Hissong et al. |
| 5,906,606 | A | 5/1999 | Chee et al. | 6,419,648 | B1 | 7/2002 | Vitek et al. |
| 5,908,029 | A | 6/1999 | Knudson et al. | 6,425,867 | B1 | 7/2002 | Vaezy et al. |
| 5,916,213 | A | 6/1999 | Haissaguerre et al. | 6,430,426 | B2 | 8/2002 | Avitall |
| 5,916,214 | A | 6/1999 | Cosio et al. | 6,440,130 | B1 | 8/2002 | Mulier |
| 5,921,924 | A | 7/1999 | Avitall | 6,443,952 | B1 | 9/2002 | Mulier |
| 5,921,982 | A | 7/1999 | Lesh et al. | 6,447,507 | B1 | 9/2002 | Bednarek et al. |
| 5,927,284 | A | 7/1999 | Borst et al. | 6,451,013 | B1 | 9/2002 | Bays et al. |
| 5,928,191 | A | 7/1999 | Houser et al. | 6,461,314 | B1 | 10/2002 | Pant et al. |
| 5,931,810 | A | 8/1999 | Grabek | 6,461,356 | B1 | 10/2002 | Patterson |
| 5,931,848 | A | 8/1999 | Saadat | 6,464,700 | B1 | 10/2002 | Koblish et al. |
| 5,954,661 | A | 9/1999 | Greenspon et al. | 6,471,697 | B1 | 10/2002 | Lesh |
| 5,967,976 | A | 10/1999 | Larsen et al. | 6,471,698 | B1 | 10/2002 | Edwards et al. |
| 5,971,980 | A | 10/1999 | Sherman | 6,474,340 | B1 | 11/2002 | Vaska et al. |
| 5,971,983 | A | 10/1999 | Lesh | 6,475,216 | B2 | 11/2002 | Mulier |
| 5,993,447 | A | 11/1999 | Blewett et al. | 6,477,396 | B1 | 11/2002 | Mest et al. |
| 6,007,499 | A | 12/1999 | Martin et al. | 6,484,727 | B1 | 11/2002 | Vaska et al. |
| 6,012,457 | A | 1/2000 | Lesh | 6,488,680 | B1 | 12/2002 | Francischelli |
| 6,016,811 | A | 1/2000 | Knopp et al. | 6,497,705 | B2 | 12/2002 | Comben |
| 6,017,338 | A | 1/2000 | Brucker et al. | 6,502,575 | B1 | 1/2003 | Jacobs et al. |
| 6,030,379 | A | 2/2000 | Panescu et al. | 6,514,250 | B1 | 2/2003 | Jahns |
| 6,042,556 | A | 3/2000 | Beach et al. | 6,527,767 | B2 | 3/2003 | Wang et al. |
| 6,053,912 | A | 4/2000 | Panescu et al. | 6,537,248 | B2 | 3/2003 | Mulier |
| 6,056,745 | A | 5/2000 | Panescu et al. | 6,537,272 | B2 | 3/2003 | Christopherson et al. |
| 6,063,081 | A | 5/2000 | Mulier | 6,558,382 | B2 | 5/2003 | Jahns |
| 6,071,279 | A | 6/2000 | Whayne et al. | 6,584,360 | B2 | 6/2003 | Francischelli |
| 6,088,894 | A | 7/2000 | Oakley | 6,585,732 | B2 | 7/2003 | Mulier et al. |
| 6,096,037 | A | 8/2000 | Mulier | 6,595,934 | B1 | 7/2003 | Hissong et al. |
| 6,099,524 | A | 8/2000 | Lipson et al. | 6,605,084 | B2 | 8/2003 | Acker et al. |
| 6,113,592 | A | 9/2000 | Taylor | 6,610,055 | B1 | 8/2003 | Swanson et al. |
| 6,117,101 | A | 9/2000 | Diederich et al. | 6,610,060 | B2 | 8/2003 | Mulier |
| 6,120,496 | A | 9/2000 | Whayne et al. | 6,613,048 | B2 | 9/2003 | Mulier |
| 6,142,993 | A | 11/2000 | Whayne et al. | 6,623,515 | B2 | 9/2003 | Mulier et al. |
| 6,142,994 | A | 11/2000 | Swanson et al. | 6,645,199 | B1 | 11/2003 | Jenkins et al. |
| 6,152,920 | A | 11/2000 | Thompson et al. | 6,648,883 | B2 | 11/2003 | Francischelli |
| 6,161,543 | A | 12/2000 | Cox et al. | 6,656,175 | B2 | 12/2003 | Francischelli |
| 6,165,174 | A | 12/2000 | Jacobs et al. | 6,663,627 | B2 | 12/2003 | Francischelli |
| 6,217,528 | B1 | 4/2001 | Koblish et al. | 6,692,450 | B1 | 2/2004 | Coleman |
| 6,217,576 | B1 | 4/2001 | Tu et al. | 6,695,839 | B2 | 2/2004 | Sharkey et al. |
| 6,224,592 | B1 | 5/2001 | Eggers et al. | 6,699,240 | B2 | 3/2004 | Francischelli |
| 6,231,518 | B1 | 5/2001 | Grabek et al. | 6,702,811 | B2 | 3/2004 | Stewart et al. |
| 6,235,024 | B1 | 5/2001 | Tu | 6,706,038 | B2 | 3/2004 | Francischelli |
| 6,237,605 | B1 | 5/2001 | Vaska et al. | 6,706,039 | B2 | 3/2004 | Mulier |
| 6,238,347 | B1 | 5/2001 | Nix et al. | 6,716,211 | B2 | 4/2004 | Mulier |
| 6,238,393 | B1 | 5/2001 | Mulier | 6,730,082 | B2 | 5/2004 | Messing et al. |

| | | |
|---|---|---|
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 6,989,010 B2 | 1/2006 | Francischelli et al. |
| 7,029,470 B2 | 4/2006 | Francischelli et al. |
| 7,083,620 B2 | 8/2006 | Jahns et al. |
| 7,094,235 B2 | 8/2006 | Francischelli |
| 7,118,566 B2 | 10/2006 | Jahns |
| 7,128,740 B2 | 10/2006 | Jacobs et al. |
| 7,156,845 B2 | 1/2007 | Mulier et al. |
| 7,166,105 B2 | 1/2007 | Mulier et al. |
| 7,169,144 B2 | 1/2007 | Hoey et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,261,711 B2 | 8/2007 | Mulier et al. |
| 7,294,143 B2 | 11/2007 | Francischelli |
| 2002/0032441 A1 | 3/2002 | Ingle et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2003/0216733 A1 | 11/2003 | McClurken et al. |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0133251 A1 | 7/2004 | Altschuler et al. |
| 2004/0138621 A1 | 7/2004 | Jahns |
| 2004/0138656 A1 | 7/2004 | Francischelli |
| 2004/0143260 A1 | 7/2004 | Francischelli |
| 2004/0181214 A1 | 9/2004 | Garabedian et al. |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0030331 A1 | 2/2005 | Thomas et al. |
| 2005/0033280 A1 | 2/2005 | Francischelli |
| 2005/0080411 A1 | 4/2005 | Ouchi |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0256522 A1 | 11/2005 | Francischelli et al. |
| 2005/0267454 A1 | 12/2005 | Hissong |
| 2006/0009756 A1 | 1/2006 | Francischelli |
| 2006/0009759 A1 | 1/2006 | Christian |
| 2006/0015097 A1 | 1/2006 | Mulier et al. |
| 2006/0052770 A1 | 3/2006 | Mulier et al. |
| 2006/0074414 A1 | 4/2006 | Mulier et al. |
| 2006/0079888 A1 | 4/2006 | Mulier et al. |
| 2006/0142753 A1 | 6/2006 | Francischelli et al. |
| 2006/0161149 A1 | 7/2006 | Privitera et al. |
| 2006/0161151 A1 | 7/2006 | Privitera et al. |
| 2006/0217701 A1 | 9/2006 | Young et al. |
| 2007/0032786 A1 | 2/2007 | Francischelli |
| 2007/0043397 A1 | 2/2007 | Ocel et al. |
| 2007/0049923 A1 | 3/2007 | Jahns |
| 2007/0093808 A1 | 4/2007 | Mulier et al. |
| 2007/0118107 A1 | 5/2007 | Francischelli et al. |
| 2007/0118114 A1 | 5/2007 | Mulier et al. |
| 2007/0208332 A1 | 9/2007 | Mulier et al. |
| 2007/0270795 A1 | 11/2007 | Francischelli et al. |
| 2008/0015563 A1 | 1/2008 | Hoey et al. |

FOREIGN PATENT DOCUMENTS

| | | |
|---|---|---|
| EP | 0370890 | 5/1990 |
| EP | 0499491 | 8/1992 |
| EP | 0500215 | 8/1992 |
| EP | 0500289 | 8/1992 |
| FR | 2235669 | 1/1975 |
| JP | 57-117843 | 7/1982 |
| WO | 90/03152 | 4/1990 |
| WO | 90/06079 | 6/1990 |
| WO | 94/10924 | 5/1994 |
| WO | 94/10925 | 5/1994 |
| WO | 94/11059 | 5/1994 |

OTHER PUBLICATIONS

Gallagher et al., "Cryosurgical Ablation of Accessory Atrioventrical Connections: A Method for Correction of the Pre-excitation Syndrome," Circulation 55(3):471-479, 1977.

Sealy, "Direct Surgical Treatment of Arrhythmias: The Last Frontier in Surgical Cardiology," Chest 75(5):536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1):67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Throacic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5):495-504, 1988.

Cox et al., Surgery for Atrial Fibrillation; Seminars in Thoracic and Cardiovascular Surgery , vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71:483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4):I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?"PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thrac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1); I-493. #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997; 12:18-13.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Hurst J. Willis, M.D., et al., "Surgical Treatment of Cardiac Arrhythmias (The Maze Procedure)".

Forty-Four Multiple Diseases; The Heart, Artheries, and Veins, 7.sup.th Edition, vol. 2, 1990.

Mulier et al., Patent Application "Method and Apparatus for RF Ablation", filed Sep. 8, 1994 (U.S. Appl. No. 08/302,304).

Mulier et al., Patent Application "Method and Apparatus for RF Ablation", filed Sep. 8, 1994 (U.S. Appl. No. 08/303,246).

Mulier et al., Patent Application "Fluid-Assisted Electrocautery Device", filed Feb. 22, 1995 (U.S. Appl. No. 08/393,082).

Mulier et al., Patent Application "Method and Apparatus for RF Ablation", filed Sep. 8, 1994 (U.S. Appl. No. 09/955,496).

"The Maze Procedure", *Cardiovascular Device Update,* vol. 1, No. 4, Jul. 1995, pp. 2-3.

Japanese Patent Office Official Action, mailed Apr. 4, 2001 (4 pgs.); Translation provided in patent application.

Reidenbach et al, "A New Method . . . Currents", Biomed Technik, 23 (1978), p. 71-74.

"Differential Response of Normal and Tumor Microcirculation to Hyperthermia," by T.E. Dudar et al, Cancer Research, vol. 44, Feb. 1984, pp. 605-612.

"Progress in Hyperthermia?," by J.R. Oleson, Int. J. Radiation Oncology, Biology, Physics, vol. 20, (Feb. 1991), p. 1143-1144.

"Percutaneous Transperineal Prostate Cryosurgery Using Transretal Ultrasound Guidance: Animal Model," by G. Onik et al., Urology, vol. 37, No. 3, (Mar. 1991) p. 277.

"Physical and Dynamic Characteristics of DC Ablation in Relation to the Type of Energy Delivery and Catheter Design," by Robert Lemery et al., PACE, vol. Jul. 1991, pp. 1158-1198.

"Basic and Clinical Studies of Local Hypothermia For Prostatic Cancer,"0 by Masataka Hirai, Nippon Hinyokika Gakkai Zasshi, vol. 83, No. 5, May 1992, pp. 597-604.

"Interstitial Laser Hyperthermia," by A. Masters et al., Seminars in Surgical Oncology, vol. 8, (1992), pp. 242-249.

"Prediction of Treatment Temperatures in Clinical Hyperthermia of Locally Advanced Breast Carcinoma: The Use of Contrast Enhanced Computed Tomography," by H. Lyng et al., Int. J. Radiation Oncology, Biol. Phys., vol. 26, (Jan. 1993), pp. 451-457.

"Thermometry of Interstitial Hyperthermia Given as an Adjuvant to Brachytherapy for the Treatment of Carcinoma of the Prostate," by S. D. Prionas et al., Int. J. Radiation Oncology, Biol. Phys., vol. 28, (Sep. 1993), pp. 151-162.

"Transurethral Radio Frequency Thermomtherapy for Symptomatic Benign Prostatic Hyperlasia," by A. Corica et al., Eur Urol, vol. 23, 1993, pp. 313-317.

"Benign Prostatic Hypertrophy Treatment by Transurethral Radiofrequency Hyperthermia with Thermex II," by J.L. Viguier et al., Eur Urol, vol. 23, 1993, pp. 318-321.

"Transurethral Thermotherapy of the Benign Prostate Hypertrophy Controlled by Radiometry," by G. Belot et al., Eur Urol, vol. 23, 1993, pp. 326-329.

"Transurethral Needle Ablation (TUNA) of the Prostate Using Low-Level Radiofrequency Energy: An Animal Experimental Study," by B. Goldwasser et al., Eur. Urol, vol. 24, 1993, pp. 400-405.

"Needle Ablation Using Radio Frequency Current as a Treatment for Benign Prostatic Hyperplasia: Experimental Results in ex vivo Human Prostate," by J. Ramon et al., Eur Urol, vol. 23, 1993, pp. 406-410.

"Transurethral Needle Ablation (TUNA): Thermal Gradient Mapping and Comparison of Lesion Size in a Tissue Model and in Patients with Benign Prostatic Hyperplasia," by J.S. Rasor et al., Eur Urol, vol. 24, 1993, pp. 411-414.

"Transuretheral Needle Alation (TUNA): Safety Feasibility, and Tolerance of a New Office Procedure for Treatment of Benign Prostatic Hyperplasia," by C.C. Schulman et al., Eur Urol, vol.. 24, 1993, pp. 415-423.

"Cooled Tip Ablation Results in Increased Radiofrequency Power Delivery and Lesion Size," PACE, vol. 17, Apr. 1994, Part II, p. 782.

"Barrier to Drug Delivery in Solid Tumors," by R.K. Jain, Scientific American, vol. 271, No. 1, (Jul. 1994), pp. 58-65.

"Hyperthermia in Cancer Therapy: Where Are We Today and Where Are We Going?" by R. A. Steeves, Bull. NY Acad. Med. (U.S.) vol. 68, No. 2, Mar.-Apr., pp. 341-350.

Abstract 832, "Hydro-Ablation: A New Method for Trans-Catheter Radiofrequency Ablation," by S.W. Adler, et al., Eur.J.C.P.E., vol. 4, No. 2, Jun. 1994.

Abstract 165, "Comparison of Radiofrequency (RF) Versus Microwave (MW) Energy Catheter Ablation of the Bovine Ventricular Mycardium," by L..A. Pires, M.D. et al., PACE, vol. 17, Apr. 1994, Part II.

Abstract 166, "Developing and Testing a Feedback Control System for Microwave Ablation: In Vitro and In Vivo Results," by P.J. Wang, M.D. et al, PACE, vol. 17, Apr. 1994, Part II.

Abstract 168, "Laser and Radiofrequency Catheter Ablation of Ventricular Myocardium in Dogs: A Comparative Test," by S. Enders, M.D. et al, PACE, vol. 17, Apr. 1994, Part II.

Abstract 0872, "Radiofrequency Delivery Through an Endocardial Cooled Catheter Results in Increased Lesion Size," by R. Ruffy et al, University of Utah, Salt Lake City, UT.

Abstract 0873, "Porous Metal Tipped Catheter Produces Larger Radiofrequency Lesions Through Tip Cooling," by D. Bergau et al, Children's Hospital, Boston, MA.

Abstract 287, "Comparsion of Transesophageal Echocardiographic Guidance of Transseptal Left Heart Catheterization During Mitral Valvuloplasty and Radiofrequency Ablation of Left-Sided Accessory Pathways," by K.J. Tucker, M.D. et al, PACE, vol. 17, Apr. 1994, Part II.

Abstract 288, "Microwave Catheter Ablation via the Coronary Sinus: The Need for Power and Temperature Regulation?," by P.J. Wang, M.D. et al, PACE, vol. 17, Apr. 1994, Part II.

Abstract 290, "Electrode Temperature During Radiofrequency Catheter Ablation Procedures: Relationship to Ablation Target and Ablation Result," by H. Calkins, M.D. et al, PACE, vol. 17, Apr. 1994, Part II.

Abstract 485, "Comparison of Tissue Temperature and Lesion Size in Radiofrequency Ablation Using Saline Irrigation with a Small Versus Large Tip Electrode in a Canine Thigh Muscle Preparation," by H. Nakagawa, M.D. et al, PACE, vol. 17, Apr. 1994, Part II.

Abstract 487, "Intramural Ablation Using Radiofrequency Energy Via Screw-Tip Catheter and Saline Electrode," by M.F. Hoey MS, et al, PACE, vol. 17, Apr. 1994, Part II.

Abstract 1291, "Increase in the Lesion Size and Decrease in the Impedance Rise with a Saline Infusion Electrode Catheter for Radiofrequency Catheter Ablation," by S.K. Stephen Huang et al., Circulation, vol. 80, No. 4, Oct. 1989.

Abstract 121, "Tissue Temperatures in Radiofrequency Ablation Using a Saline Irrigated Electrode Versus Temperature Monitoring in a Canine Thigh Muscle Preparation," by H. Nakagawa et al., Abstracts from the 67th Scientific Sessions.

"Use of Saline Infusion Electrode Catheter for Improved Energy Delivery and Increased Lesion Size in Radiofrequency Catheter Ablation," by R.S. Mittleman et al., PACE, May 1995, Part I.

Abstract 705-5, "Comparison of Radiofrequency Lesions in the Canine Left Ventricle Using a Saline Irrigated Electrode Versus Temperature Control," by H. Nakagawa et al., JACC, Feb. 1995, p. 42A.

Abstract 777-I, "Effective Delivery of Radiofrequency Energy Through the Coronary Sinus without Impedance Rise Using a Saline Irrigated Electrode," by H. Nakagawa et al., JACC, Feb. 1995, p. 293A.

Abstract 22, "Tip Temperature is not an Indicator of Intramyocardial Temperatures During Radiofrequency Catheter Ablation," by Sean Mackey, MD, et al, PACE, vol. 17, Apr. 1994, Part II.

PEN-TYPE ELECTROSURGICAL INSTRUMENT

CROSS-REFERENCE TO RELATED APPLICATIONS

This application is a continuation of U.S. patent application Ser. No. 11/230,839, filed Sep. 20, 2005, now U.S. Pat. No. 7,166,105, which is a continuation of U.S. patent application Ser. No. 10/883,178, filed Jul. 1, 2004, now U.S. Pat. No. 6,949,098, which is a continuation of U.S. patent application Ser. No. 10/411,921, filed Apr. 11, 2003, now U.S. Pat. No. 6,764,487, which is a continuation of U.S. patent application Ser. No. 09/955,496, filed Sep. 18, 2001, now U.S. Pat. No. 6,585,732, which is a continuation of U.S. patent application Ser. No. 09/580,228, filed May 26, 2000, now U.S. Pat. No. 6,358,248, which is a continuation of U.S. patent application Ser. No. 09/236,034, filed Jan. 22, 1999, now abandoned, which is a continuation of U.S. patent application Ser. No. 08/556,784, filed Nov. 2, 1995, now U.S. Pat. No. 5,897,553, which is a continuation-in-part of U.S. patent application Ser. No. 08/393,082, filed Feb. 22, 1995, now U.S. Pat. No. 6,063,081, which applications are incorporated herein by reference.

FIELD OF THE INVENTION

This invention relates generally to the field of medical instruments, and more particularly relates to an electrocautery device.

BACKGROUND OF THE INVENTION

Various types of electrocautery devices for incising and cauterizing body tissue are known and used in the medical field. Typically, such devices include a conductive tip or needle which serves as one electrode in an electrical circuit which is completed via a grounding electrode coupled to the patient. Incision of tissue is accomplished by applying a source of electrical energy (most commonly, a radio-frequency generator) to the tip. Upon application of the tip to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

It is widely recognized in the prior art that the often substantial amount of smoke produced by electrocauterization of tissue is at least unpleasant, and in some cases distracting or even hazardous to the operator and other attending medical personnel. As a result, it has been proposed, and is common, to provide an electrocautery device with smoke-aspirating capabilities, such that the smoke produced from electrocauterization is quickly withdrawn from the area of incision. Smoke aspiration may be accomplished by providing, in the handle of the electrocautery device near the electrocautery tip/electrode, an inlet port to be coupled to a vacuum or suction source. Examples of this are described in U.S. Pat. No. 4,307,720 to Weber, Jr., entitled "Electrocautery Apparatus and Method and Means for Cleaning the Same;" in U.S. Pat. No. 5,242,442 to Hirschfeld, entitled "Smoke Aspirating Electrosurgical Device;" and in U.S. Pat. No. 5,269,781 to Hewell, entitled "Suction Assisted Electrocautery Unit."

It has also been recognized in the prior art that the accumulation of coagulated blood, tissue rubble, and other debris on the electrode/tip of an electrocautery device can present a problem for the operator, necessitating the periodic cleaning of the tip, e.g., by wiping the tip over sterilized gauze or the like. This is generally regarded as undesirable, since the need to clean the electrode/tip tends to interrupt the incision procedure and increases the risks associated with contamination of the tip or the incision, damage to the tip, injury to the operator, and the like. To address this problem, it has been proposed in the prior art to provide an electrocautery instrument in which the electrode/tip is in slidable engagement with the instrument's handle, such that when the tip is retracted into the hand, any adhering debris automatically scraped off onto the tip of the handle. Such an instrument is proposed in the above-referenced Weber, Jr. '720 patent. While this arrangement may have some benefit, it still may be necessary to wipe off the tip of the handle once the tip is retracted. It is believed that a more direct and effective approach to the problem would be to reduce the amount of debris created during the electrocautery process, thereby eliminating or at least reducing the need to clean the electrode/tip.

Atrial fibrillation is the condition where the normal rhythmic contractions of the heart are replaced by rapid irregular twitchings of the muscular heart wall. At least 1 million people in the U.S. suffer from atrial fibrillation. There are at least three detrimental side effects that occur during atrial fibrillation: a rapid irregular heartbeat; impaired cardiac hemodynamics due to a loss of AV synchrony; and an increased vulnerability to thromboembolism. Surgical Treatment of Cardiac Arrhythmias, by Willis Hurst, pg. 867.

The typical treatment for atrial fibrillation has been to give the patient drugs. For most patients with atrial fibrillation, this therapy has been only moderately effective and has typically produced undesirable side effects.

In view of the problems with drug therapy to treat atrial fibrillation, it has been recognized as desirable to find a surgical treatment that would permanently cure atrial fibrillation. *Cardiovascular Device Update*, July 1995, pg. 1. Although radiofrequency catheter ablation (RFCA) has proven to be a safe and effective way of treating the most benign causes of supraventricular tachycardia (SVT), such as Wolff-Parkinson-White and AV nodal re-entry tachycardia, using ablation to treat atrial fibrillation has proven to be challenging. Id.

The so called "maze" procedure has been developed to treat atrial fibrillation. In the "maze" procedure, incisions are made into the right and left atria via an open chest surgical procedure. These incisions are located to interrupt all the potential re-entry circuit patterns that could occur in the atria and cause atrial fibrillation. The clinical success with the "maze" procedure has been good.

A problem with the "maze" procedure is that it requires open chest surgery which is undesirable. It has been recognized that it would be desirable to duplicate the "maze" procedure with ablation. Id. at pg. 3. This would allow the possibility of performing a "maze"-like procedure thoracoscopically. However, it has also been recognized that current ablation technology has not developed to allow the "maze" procedure to be duplicated with ablation. Id.

A problem with prior art ablation has been that the ablating tip, if left in contact with a piece of tissue for too long, will burn through and perforate the tissue. In many applications, it has proven difficult to balance leaving an ablating tip in position on a piece of tissue for a sufficient time to allow the tissue to be ablated but not leave it in place for a length of time to burn through and thereby perforate the tissue.

Another problem with prior art ablation devices is that if the ablating tips are left in contact with the tissue too long, the tip "sticks" to the tissue being ablated. In removing the tip, large portions of tissue are often removed attached to the tip. This is not only a result to be avoided because of the tissue damage, but it is time consuming and irritating to the physician. These are clearly problems to be avoided.

SUMMARY OF THE INVENTION

In view of the foregoing considerations, the present invention is directed to an improved electrocautery instrument.

In accordance with one aspect of the invention, the electrocautery electrode/tip is implemented with a hollow, conductive tube terminating at its distal end in a ball point type tip. Conductive fluid is applied to the proximal end of the hollow electrode/tip, and expelled from the distal end thereof during electrocautery. The ball point distal tip allows the distal tip to be directly applied to the tissue and "rolled" or slid along the tissue. This allows the distal tip to be moved across the tissue without dragging or snagging on the tissue. In addition, the conductive fluid expelled from the distal tip further lubricates the distal tip as it moves across the tissue.

In accordance with another aspect of the invention, the conductive fluid emanating from the electrode/tip conducts the RF electrocautery energy away from the distal tip so that it is primarily the fluid, rather than the distal tip that actually accomplishes the cauterizing of tissue. That is, the fluid serves as a "virtual" electrocautery electrode. Since it is the fluid, rather than the distal tip that cauterizes, coagulates and ablates, no burns or perforations are made to the tissue, reducing the amount of debris at the site of ablation. Also, the flow of fluid through the electrode/tip tends to keep the distal tip clean and cool.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
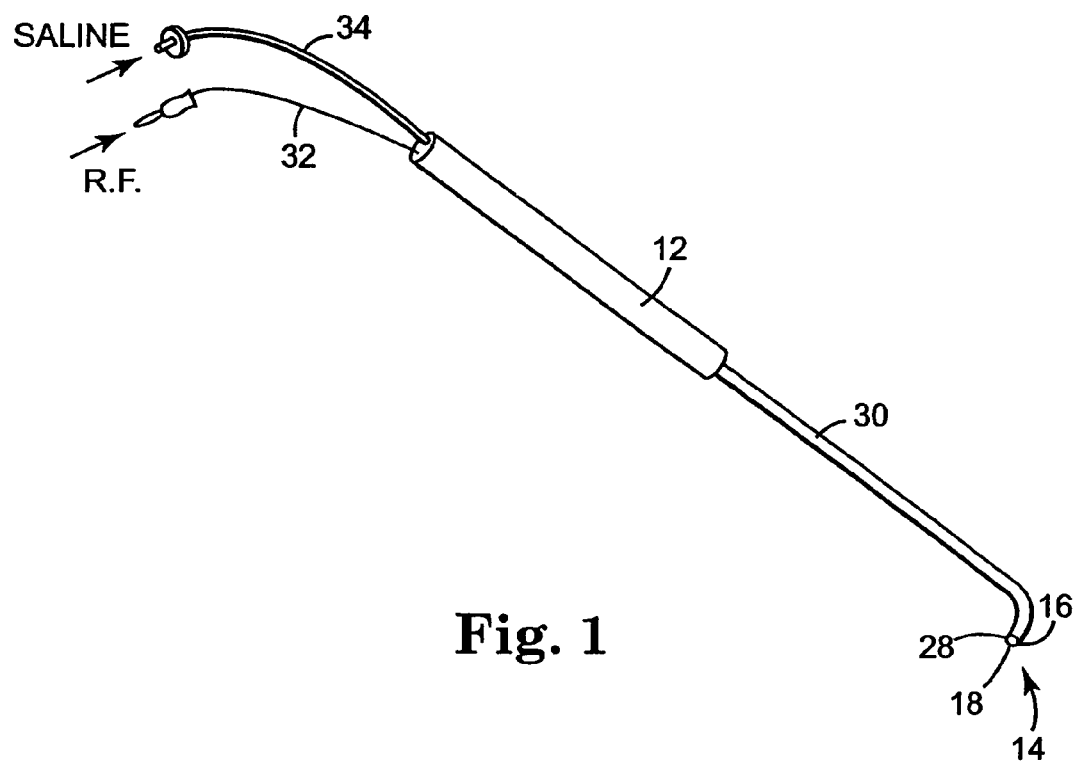
FIG. 1 is a perspective view of an electrocautery instrument in accordance with one embodiment of the invention.

Referring to FIG. 1, there is shown a perspective view of a fluid-assisted electrocautery device 10 in accordance with one embodiment of the invention. Electrodcautery device 10 comprises a handle 12 and an electrocautery electrode/tip 14. Handle 12 is preferably made of a sterilizable, rigid, and non-conductive material, such as nylon or the like. Electrode/tip 14 is attached to handle 12.

Figure 3:
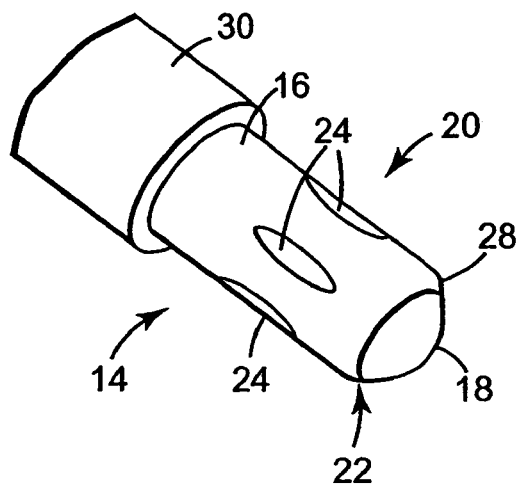
FIG. 3 is an enlarged perspective view of the distal end of the electrocautery device of FIG. 1 showing the electrode/tip.
Figure 4:
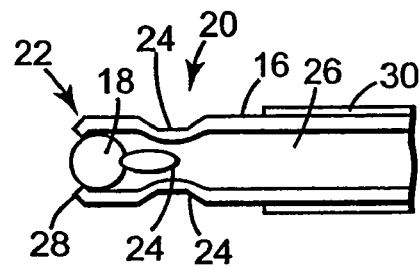
FIG. 4 is a cross-sectional view of the electrode/tip of the device of FIGS. 1, 2 and 3.

In accordance with one aspect of the invention, electrode/tip 14 is preferably implemented using a hollow cylindrical tube 16 with a "ball point" at its distal end, as shown in the greatly enlarged perspective and cross-sectional views of FIGS. 3 and 4, respectively. As can be seen, a ball 18 is retained in a cavity formed by crimping metal tube 16 around ball 18. Both ball 18 and tube 16 are preferably made of an electrically conductive metal such as stainless steel. Tube 16 is crimped both proximal and distal to ball 18 at 20 and 22, respectively.

Ball 18 may have any diameter but balls 18 having diameters of from about 1 to about 5 mm have been found to be particularly effective for ablating. Tube 16 must have a diameter corresponding to the diameter of ball 18 as explained herein. Consequently, tube 16 preferably has an internal diameter, particularly at its distal end, of from about 1 to about 5 mm.

Crimping may be accomplished by a number of techniques including but not limited to placing a series of "crimps" 24 around the periphery of tube 16 that are directed toward the interior 26 of tube 16. In addition, the distal end 28 of tube 16 is "crimped" by rounding it toward the interior 26 of tube 16. In this way, ball 18 is retained between the "crimps" 24 and the rounded distal end 28. Crimping should be done so that a portion of ball 18 extends distally beyond distal end 28.

Tube 16 preferably has in interior 26 diameter slightly larger than the diameter of ball 18. In any case, after crimping as described above, the portion of tube 16 surrounding ball 18 should have a slightly larger internal diameter than ball 18. This allows ball 18 to freely rotate between crimps 24 and distal end 28 and still be retained at electrode/tip 14.

An electrical insulator 30 preferably surrounds tube 16 along substantially its entire length, terminating a short distance from distal end 28. Insulator 30 prevents accidental cautery from taking place at locations other than electrode/tip 14 if tube 16 should inadvertently contact patient tissue during a procedure.

Two connections are made to electrocautery device 10. One terminal (e.g., positive) of a radio-frequency (RF) generator (not shown in FIG. 1) is electrically coupled to electrode/tip 14 via a wire 32 attached to tube 16. Contact between ball 18 and tube 16, as will be described in more detail hereafter, provides electrical potential to ball 18.

Figure 2:
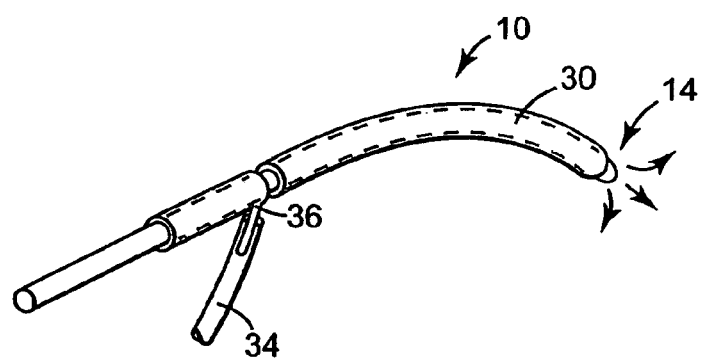
FIG. 2 is a perspective view of the invention separated from the handle.

A source of fluid to be expelled from electrode/tip 14 is coupled to tube 16 via a flexible input line 34. Input line 34 is preferably a tube or hose. Conductive fluid is provided under pressure through tube 16 to the electrode/tip 14. The conductive fluid is introduced to tube 16, as shown in FIG. 2, through input line 34 that is connected to a fluid inlet port 36 on tube 16. Conductive fluid passes from inlet line 34 through fluid inlet port 36 into tube 16 and is communicated along the length of tube 16 to electrode/tip 14 to be expelled from the distal end thereof. This creates a so-called "virtual electrode" for performing electrocautery.

The infusion of conductive fluid simultaneously with the application of RF energy is discussed in further detail in: U.S. patent application Ser. No. 08/113,441 entitled "Method and Apparatus for R-F Ablation," filed on Aug. 27, 1993 in the name of Peter M. J. Mulier and Michael F. Hoey, in U.S. patent application Ser. No. 08/303,246, entitled "Method of Apparatus for RF Ablation," filed on Sep. 8, 1994 in the name of Peter M. J. Mulier; in U.S. patent application Ser. No. 08/302,304 entitled "Method and Apparatus for RF Ablation," filed in the name of Peter M. J. Mulier and Michael F. Hoey on Sep. 8, 1994 and in U.S. patent application Ser. No. 08/393,082 entitled "Fluid Assisted Electrocautery Device", filed in the name of Peter M. J. Mulier and Michael F. Hoey on Feb. 22, 1995. The foregoing '441, '246, '304 and '082 applications (hereinafter collectively referred to as "the RF ablation applications") are each commonly assigned to the assignee of the present invention, and incorporated by reference herein in their respective entireties.

As described in the RF ablation patent applications, the infusion of conductive fluid into the area of application of RF energy creates a "virtual electrode," the size and shape of which can be controllably modified, and which can be rendered more or less conductive, thereby modifying the spread of RF energy. By varying such factors as the RF energy and duration, the rate of infusion of conductive liquid, and the conductivity of the infused solution, the size, shape, and intensity of the "virtual electrode"—i.e., the intensity of thermal production in the area, can be controlled. In the case of the electrocautery device in accordance with the present invention, application of the conductive solution during the application of RF energy further assists by preventing overheating of the electrode/tip, extending the point at which burning or charring of tissue would otherwise normally occur. To enhance this effect, it is contemplated that the solution being infused may first be cooled.

Conductive solutions believed to be suitable for establishing the virtual electrode include saline, saturated saline, and Ringer's solution, among others. Regarding the source of conductive fluid, it is contemplated that a conventional pump may be coupled to input line 34. Alternatively, it is contemplated that a small, pre-pressurized canister of conductive solution may be used, such that no pump is required. In one embodiment, handle 12 may be configured to receive such a pressurized canister therein, eliminating the need for input line 34.

In addition, a dye may be mixed with the conductive fluid to make the fluid more visible during the procedure using the device 10. Examples of such a dye include, but are not limited to methylene blue.

It is desirable to provide the conductive fluid to electrode/tip 14 under pressure that is controlled. In particular, it is important not to have a flow rate that allows conductive fluid to flow excessively out of the distal end 28 of electrode/tip 14. Excessive fluid flow has been shown to spread the electrical current density over a large area of the tissue thereby minimizing, and in some cases preventing, the ablation effect.

In use, electrical potential is applied to tube 16 from a radio-frequency (RF) generator as described above. Since tube 16 is made of an electrically conductive metal, the entire tube 16 will be at an electrical potential determined by the radio-frequency (RF) generator. Conductive fluid is supplied under pressure to the device 10 so that the conductive fluid is expelled from electrode/tip 14 around ball 18.

The user of electrocautery device 10 places electrode/tip 14 at an area to ablate and moves the electrode/tip 14 across the tissue by ball 18 contacting the tissue. Ball 18 may either roll or be slid across the tissue. The fluid expelled from the distal end 28 lubricates the tissue and facilitates the movement of ball 18 across the tissue regardless of whether ball 18 rolls or slides across the tissue.

In vitro experiments have shown the following: The larger the diameter of ball 18, the wider and deeper the ablation "track" created on the tissue; Moving the electrode/tip 14 slowly across the tissue creates deeper lesions than if electrode/tip 14 is moved quickly; and the flow rate of conductive fluid through device 10 and out of electrode/tip 14 should be adequate to wet and lubricate the surface of the tissue but should not be so high as to spread across the tissue and spread the electrical current density necessary to perform the ablation. As examples of desirable flow rates of conductive fluid through the device 10, with a radio-frequency (RF) generator at 50 Watts, a flow rate of about between 0.5 and 2 cc/minute was shown to be adequate and with a radio-frequency (RF) generator at 25 Watts, a flow rate of about between 1 and 2 cc/minute was shown to be adequate. Other flow rates in these power ranges or these or different flow rates for other power settings may also be used as will be clear with practice using the invention. The examples given above being given for the purpose of illustration and are not intended to be limiting.

The device 10 may be particularly used in connection with the so called "maze" procedure described above to ablate an area of the heart to interrupt all the potential re-entry circuit patterns that could occur in the atria and cause atrial fibrillation. The device 10 could also be used advantageously to remove hemorrhoids or varicose veins or stop esophageal bleeding to name but a few possible uses. The device removes the risk of perforation commonly found with other types of cautery, is easy to "write" with and allows deep and wide penetration and subsequently ablation.

Because of its similarity to a ball point pen, the invention provides an electrocautery device 10 that is easy to "write" with. That is, it is easy to move the distal elected/tip 14 across the tissue to be ablated because the ball 18 rolls across the tissue. In addition, by expelling fluid from electrode/tip 14, ball 18 also slides across the tissue being ablated.

Although in the embodiment of FIG. 1, wire 32 and input line 34 are depicted separately, it is contemplated that these connections to device 10 may be consolidated into a single line having a fluid-conducting lumen therein for input of conductive solution alongside an insulated electrical conductor.

Figure 5:
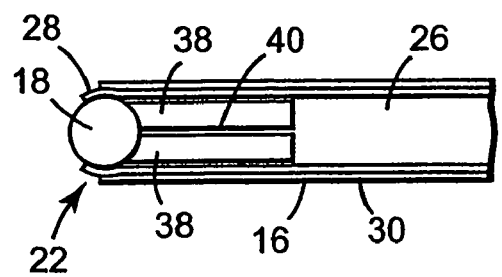
FIG. 5 is a cross-sectional view of another embodiment of electrode/tip of the invention.

Various alternate configurations of electrode/tip 14 are also contemplated. In one embodiment shown in FIG. 5, ball 18 is enclosed within tube 16 at the distal end 28 of tube 16. However, instead of having crimps 24 proximal to ball 18, a block 38 is placed proximal to ball 18 within tube 16. Block 38 preferably has a central lumen 40 exiting from its proximal to its distal end to allow fluid in the interior of tube 16 to pass to ball 18 where it may be expelled from distal end 28. In all other ways, this embodiment is identical to the preferred embodiment described above.

Ball 18 may also be made of a porous, electrically conductive material. In this embodiment, the porous nature of ball 18 allows fluid to not only pass around ball 18 to be expelled from distal end 28, but also allows fluid to pass through ball 18 to be expelled.

In an alternate embodiment, ball 18 may be replaced with a non-spherical contact element such as an electrically conductive elongated plug. In this embodiment, the plug would still be retained in tube 16 at the distal end 28 of tube 16 so that fluid can pass around the plug to expelled from the distal end 28. The plug would be retained by any means described above including, but not limited to, crimps 24 and the rounded distal end 28. However, because the plug is not spherical, the plug can not roll as it is moved in contact across the tissue to be ablated. Instead, the plug will slide across the tissue. In this embodiment, the plug may also be made of an electrically conductive porous material.

Although the invention has been described in connection with using a conductive fluid to create a virtual electrode for electrode/tip 14, it is clear that many of the advantages of the invention such as the smooth flow of electrode/tip 14 will also be produced with the conductive fluid replaced with non-conducting fluid such as pure water. Therefore, it is also within the scope of the invention to include the use of a non-conducting fluid.

In addition, if desired, a suction tube may be added to the device 10 to allow smoke or excess fluid to be removed from the surgical field. Such a suction tube is described in the '082 application described above, the teachings of which have been incorporated by reference herein.

Further, tube 16 may be made of an electrically insulating material except for a portion at its distal end that comes in contact with ball 14. This portion of tube 16 that comes in contact with ball 14 should be electrically conducing. In this embodiment, wire 24 extends to this electrically conducting portion of tube 16.

From the foregoing detailed description of a specific embodiment of the invention, it should be apparent that a method and apparatus for performing fluid-assisted electrocautery of body tissue has been disclosed, wherein fluid delivered out of a hollow electrocautery electrode/tip creates a virtual electrode which incises and cauterizes the tissue.

Although a specific embodiment of the invention has been described herein, this has been done solely for the purposes of illustrating various aspects of the invention, and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims, which follow.

What is claimed is:

1. A method of creating an ablation lesion along a length of atria tissue comprising:
   creating an opening into a patient's chest;
   providing an ablation device comprising an electrode coupled to a handle;
   inserting the electrode through the opening into the patient's chest;
   positioning the electrode adjacent atria tissue to be ablated;
   supplying radiofrequency energy via a radiofrequency generator to the electrode; and
   sliding the electrode along the length of atria tissue without snagging the atria tissue while continuing the supplying of radiofrequency energy to create an ablation lesion that interrupts one or more potential re-entry circuit patterns that could cause atrial fibrillation.

2. The method of claim 1, further comprising supplying about 50 Watts radiofrequency energy.

3. The method of claim 1, further comprising supplying about 25 Watts radiofrequency energy.

4. The method of claim 1, wherein the atria tissue is right atria tissue.

5. The method of claim 1, wherein the atria tissue is left atria tissue.

6. The method of claim 1, further supplying a fluid to lubricate the tissue.

7. The method of claim 1, further supplying a fluid to wet the tissue.

* * * * *